United States Patent [19]

Matsumoto et al.

[11] Patent Number: 4,723,012
[45] Date of Patent: Feb. 2, 1988

[54] DESMOSINE DERIVATIVES HAVING A DISULFIDE BOND AND PREPARATION OF ARTIFICIAL ANTIGEN USING THE SAME

[75] Inventors: Takashi Matsumoto, Stockholm, Sweden; Takashi Okada; Shigenobu Mizusaki, both of Tokyo, Japan

[73] Assignee: Japan Tobacco Inc., Tokyo, Japan

[21] Appl. No.: 839,576

[22] Filed: Mar. 14, 1986

[30] Foreign Application Priority Data

Mar. 25, 1985 [JP] Japan .................................. 60-58152

[51] Int. Cl.$^4$ .......................................... C07D 401/12
[52] U.S. Cl. .................................... 546/261; 546/335; 546/275; 530/387; 435/7
[58] Field of Search ................................ 546/261, 335

[56] References Cited

PUBLICATIONS

Mar. Advanced Org. Chem., p. 21, McGraw-Hill Book Co.
Darnule et al., "Solid-Phase Radioimmunoassay for Estimation of Elastin Peptides in Human Sera," Analytical Biochemistry (1982); 122:302–307.
Skinner et al., "The Estimation of Elastin in Fetal Tissues by Radioimmunoassay of Isodesmosine," Connective Tissue Research, 1983; 11:113–121.
Davies et al., "Urine Desmosine is Unrelated to Cigarette Smoking or to Spirometric Function," AM REV RESPIR DIS 1983; 128:473–475.
Kucich et al., "Immunologic Measurement of Elastin-Derived Peptides in Human Serum," AM REV RESPIR DIS 1983; 127:S28–S30.
Harel et al., "Desmosine Radioimmunoassay for Measuring Elastin Degradation In Vivo," AM REV RESPIR DIS 1980; 122:769–773.

*Primary Examiner*—Jane T. Fan
*Attorney, Agent, or Firm*—Schwartz Jeffery Schwaab Mack Blumenthal & Evans

[57] ABSTRACT

A novel desmosine derivative, which is useful for preparing a desmosine artificial antigen, has an activated, disulfide bond on the side chain at 3 or 5 position of the pyridinium ring. The derivative can combine with a polymer having thiel groups by a disulfide bond to form the effective artificial antigen.

3 Claims, 1 Drawing Figure

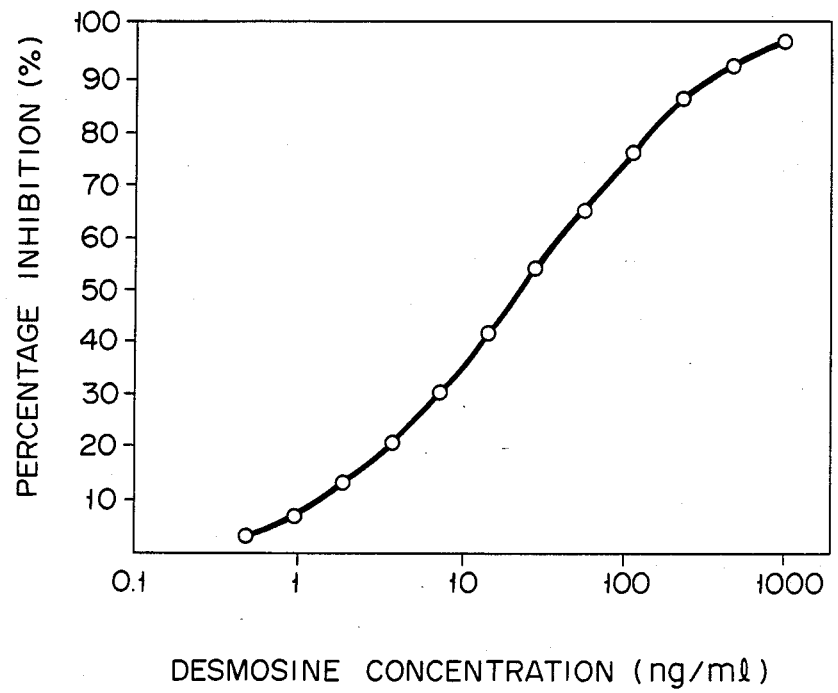

DESMOSINE DERIVATIVES HAVING A DISULFIDE BOND AND PREPARATION OF ARTIFICIAL ANTIGEN USING THE SAME

BACKGROUND OF THE INVENTION

1. Field of the Invention

This invention relates to novel desmosine derivatives and their application.

2. Description of the Prior Art

In the lungs, a balance is preserved between the elastase, one of the proteases and antielastase. Namely, as can be inferred the network of the elastic fibers of the lungs is protected by the action of the antielastase from the damages arising from its extension. When the balance is destroyed due to some cause, the elastin (elastic fibers), the main component of the lungs, undergoes an unlimited decomposition, resulting in the destruction of pulmonary cells and consequently chronic obstructive pulmonary disease (COPD). If a highly sensitive chemical analytic process is available which can determine the manner in which elastin is decomposed in the living organism, it will be possible to effectively detect changes in the morbid condition of various tissues and organs including the lungs as early as possible. When decomposed, elastin is excreted into the urine in the form of peptide containing cross-linked amino acid such as unique desmosine found in elastin alone. Consequently analysis of a quantity of desmosine excreted into the urine will ensure the discovery of the occurrence of pulmonary diseases.

Recently Harel et al, Am. Rev. Respir. Dis., Vol 122, p 769, 1980, and King et al Connect. Tissue Res., Vol 7, P 263, 1980 disclosed the process of analyzing desmosine contained in the urine by means of radioimmunoassay (RIA). However, since RIA method involves the use of radioisotopes, it presents various difficulties such as not only hazards to the human body, but also environmental pollution, difficulties in waste disposed, establishment of an extra facility required for the application of radioisotopes, and problems concerning the application period of radioisotopes due to their half-life. Consequently the RIA method involves numerous difficulties in being accepted as a general analytic method and is obstructed in rapid dissemination. Moreover, the artificial desmosine antigen developed by Harel et al or King et al is prepared by combining desmosine and protein at random using 1-ethyl-3-(3-dimethylaminopropyl)carbodiimide hydrochloride. Therefore, the artificial desmosine antigen proposed by the above-mentioned researchers gives an antibody having only an extremely low titer. Their analytic method only has the maximum merit of diluting antiserum to the extent of 200 to 250 times magnification. In this respect, too, the RIA method presents great difficulties in wide dissemination.

In view of the above-mentioned difficulties, it has become necessary to develop a new desmosine-analyzing method based on the enzymeimmunoassay (EIA). The EIA offers the advantages that less hazards are presented to the human body than RIA process when a clinical chemical examination is performed; difficulties are eliminated in dumping waste leading to environmental pollution; it is unnecessary to provide any extra facility for its application; reagents involved can be safely stored over a long period time; and wide dissemination is ensured.

Nevertheless, the EIA process is generally considered to have such an unsatisfactory detection sensitivity as is ten times lower than the RIA process. Therefore, antiserum applied to the EIA process is demanded to have an extremely high antibody titer.

SUMMARY OF THE INVENTION

It is accordingly an object of this invention to provide a novel substance which can be applied to the preparation of an artificial antigen which ensures the derivation of antidesmosine antiserum having an extremely high antibody titer value.

To attain the above-mentioned object, the present invention provides a desmosine derivative represented by the following formula:

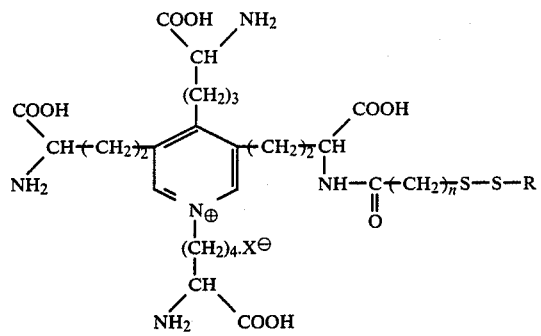

where R is an electron-attracting organic group, $X^\ominus$ is an anion, and n is an integer of 1 to 6.

Further object of the present invention is to provide a reagent for preparation of an artificial antigen intended for the production of antidesmosine antigen.

BRIEF DESCRIPTION OF THE DRAWINGS

The appended Figure is a graph showing the result of the enzymeimmunoassay of desmosine by applying the antidesmosine antiserum derived from an artificial antigen bonding a desmosine derivative according to this invention.

DETAILED DESCRIPTION OF THE PREFERRED EMBODIMENTS

The compound of this invention is a novel substance containing, as seen from Formula 1, a disulfide group in the side chain at 3 or 5 position of the pyridinium ring. In Formula I, R represents an electron-attracting organic group. Preferably, R is an aromatic group. Examples of the group R include pyridyl, azidophenyl, and phenyl.

In Formula 1, $X^\ominus$ denotes proper anions such as acetate, formate, chlorine, bromine and iodine ions. When, however, a desmosine derivative of this invention is applied as a reagent for the preparation of an artificial antigen to derive an antidesmosine antigen, a portion acting as an antigenic determinant is the cation portion, and the anion $X^\ominus$ makes no contribution to an immune response reaction. Therefore, the anion $X^\ominus$ need not be limited to the foregoing examples. In Formula I, n denotes an integer of 1 to 6, and preferably 2 to 4.

The desmosine derivative of this invention can be prepared by reacting desmosine or its salt with activated carboxylic acid represented by the formula:

A—OC—(CH₂)ₙ—S—S—R   (II)

where R and n are the same as in Formula I, and A is ethoxy group,

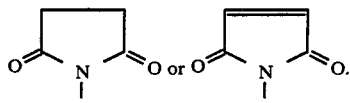

Examples of the activated carboxylic acid of Formula II are
ethoxycarbonyl-3-(2-pyridyldithio)propionate,
ethoxycarbonyl-4-(2-pyridyldithio)butytate,
ethoxycarbonyl-5-(2-pyridyldithio)valerate,
ethoxycarbonyl-6-(2-pyridyldithio)capronate,
ethoxycarbonyl-7-(2-pyridyldithio)caprylate,
N-succinimidyl-3-(2-pyridyldithio)propionate,
N-succinimidyl-4-(2-pyridyldithio)butyrate,
N-succinimidyl-5-(2-pyridyldithio)valerate,
N-succinimidyl-6-(2-pyridyldithio)capronate,
N-succinimidyl-7-(2-pyridyldithio)caprylate,
N-maleinimidyl-3-(2-pyridyldithio)propionate,
N-maleinimidyl-4-(2-pyridyldithio)butyrate,
N-maleinimidyl-5-(2-pyridyldithio)valerate,
N-maleinimidyl-6-(2-pyridyldithio)capronate,
N-maleinimidyl-7-(2-pyridyldithio)caprylate,
ethoxycarbonyl-3-(4-azidophenyldithio)propionate,
ethoxycarbonyl-4-(4-azidophenyldithio)butyrate,
ethoxycarbonyl-5-(4-azidophenyldithio)valerate,
ethoxycarbonyl-6-(4-azidophenyldithio)capronate,
ethoxycarbonyl-7-(4-azidophenyldithio)caprylate,
N-succinimidyl-3-(4-azidophenyldithio)propionate,
N-succinimidyl-4-(4-azidophenyldithio)butyrate,
N-succinimidyl-5-(4-azidophenyldithio)valerate,
N-succinimidyl-6-(4-azidophenyldithio)capronate,
N-succinimidyl-7-(4-azidophenyldithio)caprylate,
N-maleinimidyl-3-(4-azidophenyldithio)propionate,
N-maleinimidyl-4-(4-azidophenyldithio)butyrate,
N-maleinimidyl-5-(4-azidophenyldithio)valerate,
N-maleinimidyl-6-(4-azidophenyldithio)capronate and
N-maleinimidyl-7-(4-azidophenyldithio)caprylate.

According to the present invention, the reaction of desmosine with the activated carboxylic acid is carried out at 0° to 30° C. and preferably 15° to 20° C., and for 1 to 5 hours. The desmosine and the activated acid are used in a molar ratio of 1:0.5 to 1:1.5, preferably 1:1.05.

It is important that the above-mentioned reaction be performed in a phosphate buffered solution with the pH value of 5.0 to 6.5. Reaction under this pH condition causes the activated carboxylic acid to selectively react with the amino group on the side chain at 3 or 5 position of the pyridinium ring of desmosine, thereby forming an amide bond. The reaction product can be isolated by means of column chromatography as described in Example 1.

The desmosine derivative of this invention is bonded with a carrier polymer having a thiol group to prepare an antigen. Reaction between the desmosine derivative and carrier polymer is thiol-disulphide exchange reaction. This reaction causes the desmosine portion of the desmosine derivative to be bonded with the polymer carrier by the disulfide bond, with the elimination of R—SH. This process provides an artificial antigen for derivation of antidesmosine antibody. The thiol-disulfide exchange reaction is carried out at a temperature of 0° to 30° C. for a period of 1 to 5 hours, with the desmosine derivative and the carrier polymer being used in a molar ratio of 10:1 to 20:1.

The carrier polymer applied in the preparation of an artificial antigen may be natural or synthetic, provided the molecule of the polymer contains a thiol radical and has a biocompatibility. The carrier polymer includes peptide (including protein) and other polymers. Specific examples of the carrier polymer are those derived from bovine serum albumin (BSA), mouse gamma globulin (MGG), mouse serum albumin (MSA), and keyhole limpet hemocyanin by reducing their intramolecular disulfide bonds with dithiothreitol to thiols.

As seen from the formula (I), one molecule of the desmosine derivative of the invention is bonded with the carrier polymer by means of one bridge linkage without any change of the desmosine structure, particularly the other three amino acid residual groups bonded with the pyridinium ring. As a result, it is possible to provide an artificial antigen having an antigenic determinant structure fully exposed to the molecule surface. Therefore, this artificial antigen ensures the preparation of antidesmosine antiserum having an extremely high antibody titer.

EXAMPLE 1

Preparation of 4-(4-amino-4-carboxybutyl)1-(5-amino-5-carboxypentyl)-5-(3-amino-3-carboxypropyl)-3-[3-carboxy-3-{3-(2-pyridildithio)propionyl}amino]-propylpyridinium acetate Desmosine, 39 mg, was dissolved in phosphate buffered solution (0.05M, pH 5.9) containing 25 ml of 0.1 M NaCl in a triangular flask of 50 ml. Separately, 23 mg of N-succinimidyl-3-(2-pyridyldithio)propionate was dissolved in 3 ml of ethanol. The latter solution was slowly dripped in the desmosine solution. The reaction mixture was stirred for 3 hours at room temperature. After reaction, the solvent was removed by means of a rotary evaporator. The residue was poured into a column (1.5 cm in diameter and 90 cm in height) of Sephadex G-25 Super Fine available from Pharmacia Fine Chemicals Co., and eluted with an acetate buffered solution (0.1 M, pH 4.5) at the flow rate of 0.1 ml/min. The eluate was collected in test tubes at the rate of 3 ml. First, unreacted desmosine (the 26th to 29th test tubes) was eluted. Then the desmosine derivative of this invention (the 33rd to 35th test tubes) was eluted. Last, the by-products (the 37th to 40th test tubes) were eluted. The solvent was removed from the fractions containing the desmosine derivative of this invention by means of a rotary evaporator. The residue was poured into a column (2.5 cm in diameter and 91 cm in height) of Biogel P-2-(—400 mesh) available from Rio Rad Laboratories Co., and eluted with 0.1 M of acetic acid to effect separation and desaltation. After freeze-dried, 15.6 mg of light yellow solid was obtained (yield 30%). This light yellow solid was analyzed by means of ¹H NMR, mass spectrum (MS) and ultraviolet absorption spectrum (UV). The product proved to be the desired desmosine derivative having a purity of 97% or more. The analytical data obtained were as follows:

¹H NMR (solvent D₂O, internal standard DSS) (ppm): 1.40 (m,1H), 1.47 (m,1H), 1.59 (m,1H), 1.67 (m,1H), 1.89 (m,2H), 2.06 (s,3H), 1.96–2.11 (m,4H), 2.17 (m,4H), 2.78 (m,2H), 2.90 (m,4H), 3.02 (m,2H), 3.12 (t,2H), 3.73 (t,1H), 3.79 (m,1H), 3.88 (m,2H), 4.48 (t,2H), 7.30 (t,1H), 7.84 (m,2H), 8.39 (d,1H), 8.46 (s,1H), 8.52 (s,1H).

MS (m/z): 723.

UV (solvent 0.1N acetic acid) : λ (max); 236 nm, 276 nm (shoulder, 270 nm).

EXAMPLE 2

Preparation of 4-(4-amino-4-carboxybutyl)1-(5-amino-5-carboxypentyl)-5-(3-amino-3-carboxypropyl)-3-[3-carboxy-3-{3-(4-azidophenyldithio)propionyl}amino]propylpyridinium acetate Desmosine tetraacetate, 38 mg (65 μmol), was dissolved in phosphate buffered solution (0.05M, pH 5.9) containing 25 ml of 0.1 M NaCl in a triangular flask of 50 ml. Separately, 21 mg of N-succinimidyl-3-(4-azidophenyldithio)propionate was dissolved in 3 ml of dimethyformamide. The latter solution was slowly dripped in the desmosine solution. The reaction mixture was stirred for 3 hours at room temperature. After reaction, the solvent was removed by means of a rotary evaporator. The residue was poured into a column (2.5 cm in diameter and 91 cm in height) of Biogel P-2-(−400 mesh), and eluted with 0.1 M of acetic acid. The eluate was collected in a volume of 10 ml in test tubes. The fractions collected in the 23rd to 25th test tubes were freeze-dried to obtain 25 mg of the desired product as a light yellow solid.

EXAMPLE 3

Preparation of an Artificial Antigen

The intramolecular disulfide bonds of bovine gammaglobulin (BGG) was reduced by dithiothreitol to be converted into thiols according to the method described in Analytical Biochemistry, 94, 253–258 (1979). The thiolated BGG, 20 mg, was dissolved in 10 ml of a phosphate buffered solution (pH 7.5, 0.1 M) containing 0.1 M NaCl and 6 M urea. Desmosine derivative, 4.67 mg, obtained in Example 1 was added. The mixture was stirred at room temperature for 45 minutes. 15 ml of 10% trichloroacetic acid was added to the reacted solution. The mixture was subjected to centrifugal separation at a rotation rate of 3000 rpm for 10 minutes. The supernatant was taken off. 1 ml of water was added to the white precipitate and washing was carried out by centrifuge. The white precipitate was freeze-dried, producing 17 mg of the desired antigen as white powder. The bonded molar ratio between the desmosine portion of the antigen and BGG was calculated to be 10 by the process of determining the ultraviolet ray absorbance at 343 nm of the above-mentioned reacted solution to quantitatively analyze pyridine-2-thione released by the thiol-disulfide exchange reaction, with the molecular weight of thiolated BGG assumed to be 150,000.

EXAMPLE 4

Derivation of Antidesmosine Antiserum 0.3 ml of 8 M urea was dissolved in 1.45 mg of the antigen obtained in Example 3. 0.5 ml of physiological saline (0.9%) was added. The mixture was thoroughly mixed with the equivalent amount of Freund's complete adjuvant for emulsification. The preparation was injected into the six portions of the inner surfaces of the toes of each of three white male New Zealand rabbit weighing 3.5 kg. Nine days later, a second immunization was undertaken by the process of thoroughly dissolving 0.1 ml of 8 M urea in 1.53 mg of desmosine artificial antigen, adding 0.6 ml of physiological salt solution (0.9%), thoroughly mixing the mixture with the equivalent amount of Freund's incomplete adjuvant for emulsification, and subcutaneously injecting the preparation into 10 portions of the rabbit's back. Later, five immunization steps were taken every two weeks by injecting a preparation obtained by emulsifying 0.1 mg of the desmosine derivative in 100 microliters of physiological saline into the ear vein of the rabbit. All three immunized rabbits showed an increase in the antibody titer, and a dose-response curve could be drawn. Thus, it was proved that the antibody obtained from the artificial antigen prepared from the desmosine derivative of this invention was specific to desmosine. On the 11th day after the final injection (91 days after the initial immunization), the total blood collection was undertaken through the carotid artery of the rabbit which had been subjected to starvation from the day preceding the blood collection. Thus, the antidesmosine antiserum was obtained.

EXAMPLE 5

EIA for Desmosine

Desmosine was enzyme-immunoassayed using the antidesmosine antigen obtained in Example 4.

A predetermined quantity of a complex of desmosine with keyhole limpet hemocyanin, obtained by the carbodiimide method through the customary step, was coated in the wells of an EIA microplate of the 96 well type, thereby bonding the desmosine to the wells. The wells were further added with solutions of various concentrations of free desmosine to be used as analytic samples. Then an antigen-antibody reaction was carried out by progressing filling the wells with the antiserum in such a manner that the antiserum held in the 96th well was finally diluted to 30,000 times the original quantity. After reaction, the free desmosine was separated, and the antidesmosine antibody reacted with the bonded desmosine and alkaliphosphatase-labeled goat (anti-rabbit IgG) antibody were bonded together. Measurement was made of the enzyme activity of the bonded mass. The above-mentioned method determines the concentration of the free desmosine by measuring the competitive inhibition by the free desmosine against the antigen-antibody reaction between the antidesmosine antigen and the bonded desmosine. As seen from the appended chart, therefore, the application of the 30,000 times diluted antiserum ensured the determination of the minute amount ($10^{-9}$ g/ml) of desmosine. The percentage inhibition against the reaction between the bonded desmosine and antidesmosine antigen can be determined from the formula:

Percentage inhibition (%)=(A−B)/A×100 where A is enzyme activity of a desmosine-free sample (control), and B is enzyme activity of a desmosine-containing sample.

The results of the foregoing experiments prove that the antidesmosine antiserum derived from the artificial antigen bonded with the desmosine derivative of this invention can be satisfactorily applied in analysis even though the antidesmosine antiserum may be diluted over 100 times more than the conventional antiserum, namely, has an extremely high antibody titer.

What is claimed is:

1. A desmosine derivative having a formula:

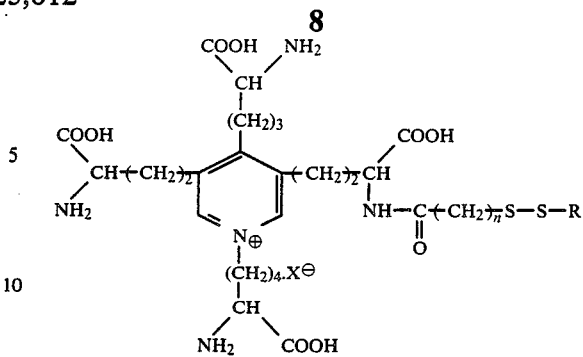
wherein R is pyridyl, azidophenyl or phenyl, X⊖ is an anion, and n is an integer from 1 to 6.
2. The desmosine derivative according to claim 1, wherein said R is 2-pyridyl, and n is 2.
3. The desmosine derivative according to claim 1, wherein said R is azidophenyl, and n is 2.
* * * * *